US00PP30514P2

(12) United States Plant Patent
Head et al.

(10) Patent No.: US PP30,514 P2
(45) Date of Patent: May 21, 2019

(54) ***DISTYLIUM* PLANT NAMED 'RLH-DM1ER'**

(50) Latin Name: *Distylium myricoides*
Varietal Denomination: RLH-DM1ER

(71) Applicants: Robert Harold Head, Seneca, SC (US); Lisa Jones Head, Seneca, SC (US)

(72) Inventors: Robert Harold Head, Seneca, SC (US); Lisa Jones Head, Seneca, SC (US)

(73) Assignee: HEAD'S SELECT, INC., Seneca, SC (US)

( * ) Notice: Subject to any disclaimer, the term of this patent is extended or adjusted under 35 U.S.C. 154(b) by 0 days.

(21) Appl. No.: 15/932,646

(22) Filed: Mar. 30, 2018

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — C. A. Whealy

(57) ABSTRACT

A new and distinct cultivar of *Distylium* plant named 'RLH-DM1ER', characterized by its low and outwardly spreading plant habit; freely branching habit, dense and bushy plant form; developing leaves that are dark green in color and becoming dark greyed green with development; flat and closely-spaced leaves; tolerance to water-saturated soil conditions; and good container and garden performance.

2 Drawing Sheets

Botanical designation: *Distylium myricoides*.
Cultivar denomination: 'RLH-DM1ER'.

BACKGROUND OF THE INVENTION

The present invention relates to a new and distinct *Distylium* plant, botanically known as *Distylium myricoides* and hereinafter referred to by the name 'RLH-DM1ER'.

The new *Distylium* plant originated from a cross-pollination in March, 2008 in Seneca, S.C. of *Distylium myricoides* 'Lucky Charm', not patented, as the female, or seed, parent with an unnamed selection of *Distylium myricoides* as the male, or pollen, parent. The new *Distylium* plant was discovered and selected by the Inventors as a single plant from within the progeny of the stated cross-pollination in a controlled environment in Seneca, S.C. in 2010.

Asexual reproduction of the new *Distylium* plant by semi-hardwood and hardwood stem cuttings in a controlled environment in Seneca, S.C. since September, 2010 has shown that the unique features of this new *Distylium* plant are stable and reproduced true to type in successive generations.

SUMMARY OF THE INVENTION

Plants of the new *Distylium* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'RLH-DM1ER'. These characteristics in combination distinguish 'RLH-DM1ER' as a new and distinct *Distylium* plant:

1. Low and outwardly spreading plant habit.
2. Freely branching habit, dense and bushy plant form.

3. Developing leaves that are dark green in color and becoming dark greyed green with development.
4. Flat and closely-spaced leaves.
5. Tolerant to water-saturated soil conditions.
6. Good container and garden performance.

Plants of the new *Distylium* can be compared to plants of the female parent, 'Lucky Charm'. Plants of the new *Distylium* differ primarily from plants of 'Lucky Charm' in the following characteristics:

1. Plants of the new *Distylium* are more low spreading than and not as upright as plants of 'Lucky Charm'.
2. Plants of the new *Distylium* are denser than and not as open as plants of 'Lucky Charm'.
3. Plants of the *Distylium* and 'Lucky Charm' differ in developed leaf color as plants of 'Lucky Charm' have olive green-colored developed leaves.

Plants of the new *Distylium* can be compared to plants of the male parent selection. Plants of the new *Distylium* differ primarily from plants of the male parent selection in the following characteristics:

1. Plants of the new *Distylium* are more low spreading than and not as mounding as plants of the male parent selection.
2. Plants of the new *Distylium* are denser than and not as open as plants of the male parent selection.
3. Plants of the *Distylium* and the male parent selection differ in developed leaf color as plants of the male parent selection have deeper green-colored developed leaves.

Plants of the new *Distylium* can also be compared to plants of *Distylium myricoides* 'Vintage Jade', disclosed in U.S. Plant Pat. No. 23,128. In side-by-side comparisons, plants of the new *Distylium* differ primarily from plants of 'Vintage Jade' in the following characteristics:

1. Plants of the new *Distylium* are more low spreading than and not as mounding as plants of 'Vintage Jade'.

2. Plants of the new *Distylium* are less vigorous than plants of 'Vintage Jade' and do not require as much pruning as plants of 'Vintage Jade'.
3. Plants of the new *Distylium* are more freely branching than plants of 'Vintage Jade'.
4. Plants of the *Distylium* and 'Vintage Jade' differ in developed leaf color as plants of 'Vintage Jade' have darker green-colored developed leaves.

BRIEF DESCRIPTION OF THE PHOTOGRAPHS

The accompanying colored photographs illustrate the overall appearance of the new *Distylium* plant showing the colors as true as it is reasonably possible to obtain in colored reproductions of this type. Colors in the photographs may differ slightly from the color values cited in the detailed botanical description which accurately describe the colors of the new *Distylium* plant.

The photograph on the first sheet is a top perspective view of a typical flowering plant of 'RLH-DM1ER'.

The photograph on the second sheet is a close-up view of a typical flowering plant of 'RLH-DM1ER'.

DETAILED BOTANICAL DESCRIPTION

The aforementioned photographs and following observations, measurements and values describe plants grown during the winter and early spring in three-gallon containers in outdoor nurseries in Park Hill, Okla. and Fort Worth, Tex. and under cultural practices typical of commercial *Distylium* production. During the production of the plants, day temperatures ranged from −5° C. to 40° C. and night temperatures ranged from −20° C. to 35° C. Plants were 3.5 years old when the photographs and the description were taken. In the description, color references are made to The Royal Horticultural Society Colour Chart, 2007 Edition, except where general terms of ordinary dictionary significance are used.

Botanical classification: *Distylium myricoides* 'RLH-DM1ER'.

Parentage:

*Female, or seed, parent.*—*Distylium myricoides* 'Lucky Charm', not patented.

*Male or pollen parent.*—Unnamed selection of *Distylium myricoides*, not patented.

Propagation:

*Type.*—By semi-hardwood and hardwood stem cuttings.

*Time to initiate roots, summer.*—About 35 to 50 days at temperatures ranging from 27° C. to 30° C.

*Time to initiate roots, winter.*—About 45 to 70 days at temperatures ranging from 16° C. to 17° C.

*Time to produce a rooted young plant, summer.*—About 65 to 90 days at temperatures ranging from 27° C. to 30° C.

*Time to produce a rooted young plant, winter.*—About three to four months at temperatures ranging from 16° C. to 17° C.

*Root description.*—Thin to medium in thickness, fibrous; close to NN155C in color becoming more brown with development.

*Rooting habit.*—Freely branching; medium density to dense.

Plant description:

*Plant and growth habit.*—Perennial evergreen shrub; low spreading plant habit; moderately vigorous growth habit.

*Branching habit.*—Freely branching habit with lateral branches potentially developing at every node; dense and bushy plant form.

*Plant height.*—About 32.5 cm.

*Plant diameter* (*area of spread*).—About 87.5 cm.

Lateral branch description:

*Length.*—About 43 cm.

*Diameter, immature.*—About 1 mm.

*Diameter, mature.*—About 7 mm.

*Internode length.*—About 2.5 cm.

*Aspect.*—About 70° to 90° from vertical.

*Strength.*—Strong; flexible when immature.

*Texture and luster.*—Pubescent, fine; scabrous; matte.

*Color, immature.*—Close to 146B becoming closer to 146A with development.

*Color, mature.*—Close to 197A to 197B.

Leaf description:

*Arrangement.*—Alternate, single.

*Length.*—About 6.75 cm.

*Width.*—About 1.9 cm.

*Shape.*—Oblong.

*Apex.*—Acuminate to cuspidate.

*Base.*—Narrowly obtuse to attenuate.

*Margin.*—Entire.

*Texture and luster, upper surface.*—Smooth, glabrous; leathery; glossy.

*Texture and luster, lower surface.*—Pubescent, fine; leathery; matte.

*Venation pattern.*—Pinnate.

*Color.*—Developing leaves, upper surface: Close to 147A. Developing leaves, lower surface: Close to 146B. Fully expanded leaves, upper surface: Close to 189A; venation, close to 146A. Fully expanded leaves, lower surface: Close to 147B; venation, close to 144A.

*Petiole.*—Length: About 6 mm. Diameter: About 1 mm. Texture and luster, upper surface: Smooth, glabrous; matte. Texture, lower surface: Pubescent, fine; scabrous; matte. Color, upper surface: Close to 146A to 146B. Color, lower surface: Close to 144A to 144B.

Flower description:

*Flower arrangement and flowering habit.*—Small single flowers arranged in terminal and axillary racemes; typically about five flowers per raceme; freely flowering habit; flowers face outwardly to upright.

*Natural flowering season.*—Early flowering habit, plants of the new *Distylium* flower during the late winter in Oklahoma and Texas; flowers last several weeks on the plant; flowers not persistent.

*Fragrance.*—None detected.

*Flower diameter.*—About 3 mm.

*Flower height, including reproductive organs.*—About 9 mm.

*Flower buds.*—Length: About 5 mm. Diameter: About 2 mm. Shape: Ovoid. Texture and luster: Pubescent; matte. Color: Close to 199A.

*Petals.*—Flowers of the new *Distylium* are apetalous.

*Sepals.*—Arrangement: Typically three to five sepals in a single whorl. Length: About 3 mm. Width: About 1.75 mm. Shape: Roughly deltoid. Apex: Acute. Base: Fused. Margin: Entire. Texture and luster, upper and lower surfaces: Smooth, glabrous; semi-glossy. Color, upper and lower surfaces: Close to 144A.

*Bracts*.—Arrangement: Typically one subtending each flower. Length: About 7.5 mm. Width: About 3 mm. Shape: Lanceolate. Apex: Acute. Base: Fused. Margin: Entire. Texture and luster, upper and lower surfaces: Pubescent; matte. Color, upper surface: Close to 145B to 145C. Color, lower surface: Close to between 199A and N199B; with cooler temperatures, tinged with close to 187A.

*Peduncles*.—Length: About 1.2 cm. Diameter: About 1.5 mm. Strength: Flexible. Texture and luster: Pubescent, fine; matte. Color: Close to 144A.

*Pedicels*.—Length: Less than 1 mm. Diameter: Less than 1 mm. Strength: Flexible. Texture and luster: Pubescent, fine; matte. Color: Close to 144A.

*Reproductive organs*.—Androecium: Stamen number: About two to eight per flower. Filament length: About 2 mm. Filament color: Close to 146D. Anther length: Less than 1 mm. Anther color: Close to 146D. Amount of pollen: None observed to date. Gynoecium: Pistil number: Two per flower. Pistil length: About 1.1 cm. Style length: About 1 cm. Style color: Close to 144A. Stigma color: Close to 144A. Ovary color: Close to 144C to 144D.

*Fruits and seeds*.—Fruit and seed development have not been observed on plants of the new *Distylium* to date.

Garden performance: Plants of the new *Distylium* have been observed to have good garden performance and to tolerate wind, water-saturated soil conditions and temperatures ranging from about −25° C. to about 43° C. and to be suitable for USDA Hardiness Zones 6B to 9.

Pathogen & pest resistance: Plants of the new *Distylium* have not been observed to be resistant to pathogens and pests common to *Distylium* plants to date.

It is claimed:

1. A new and distinct *Distylium* plant named 'RLH-DM1ER' as illustrated and described.

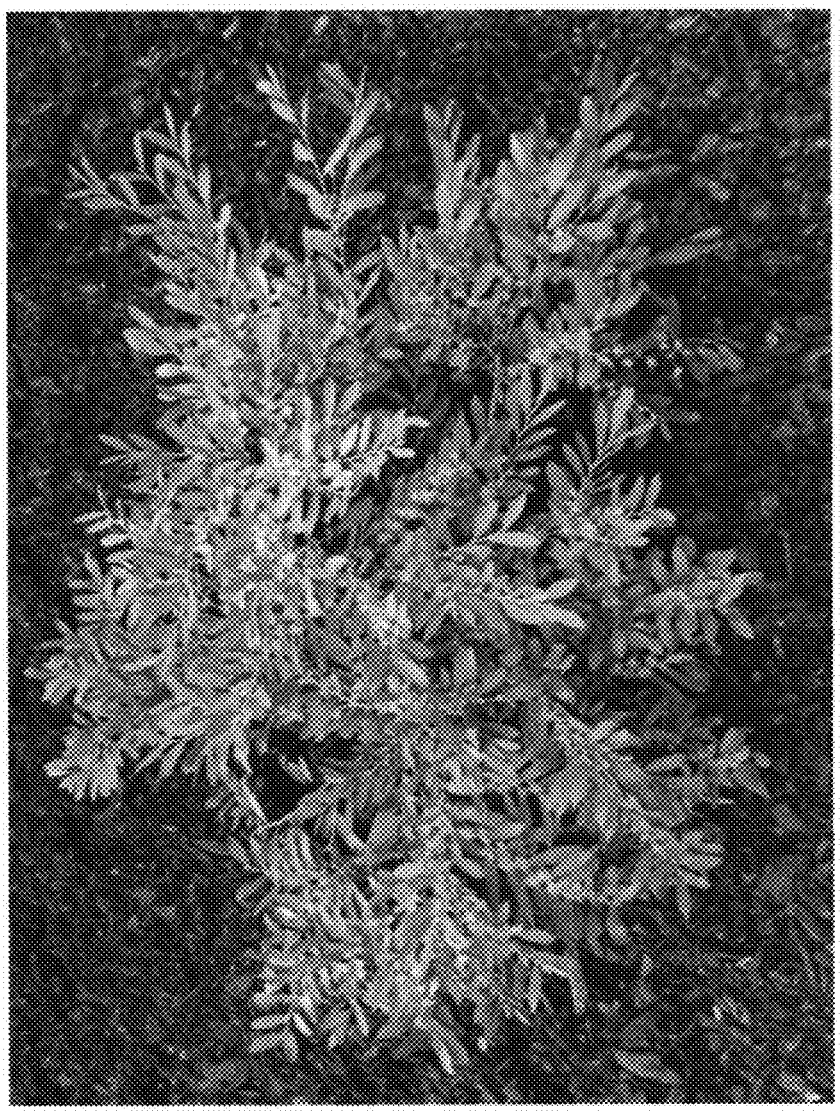

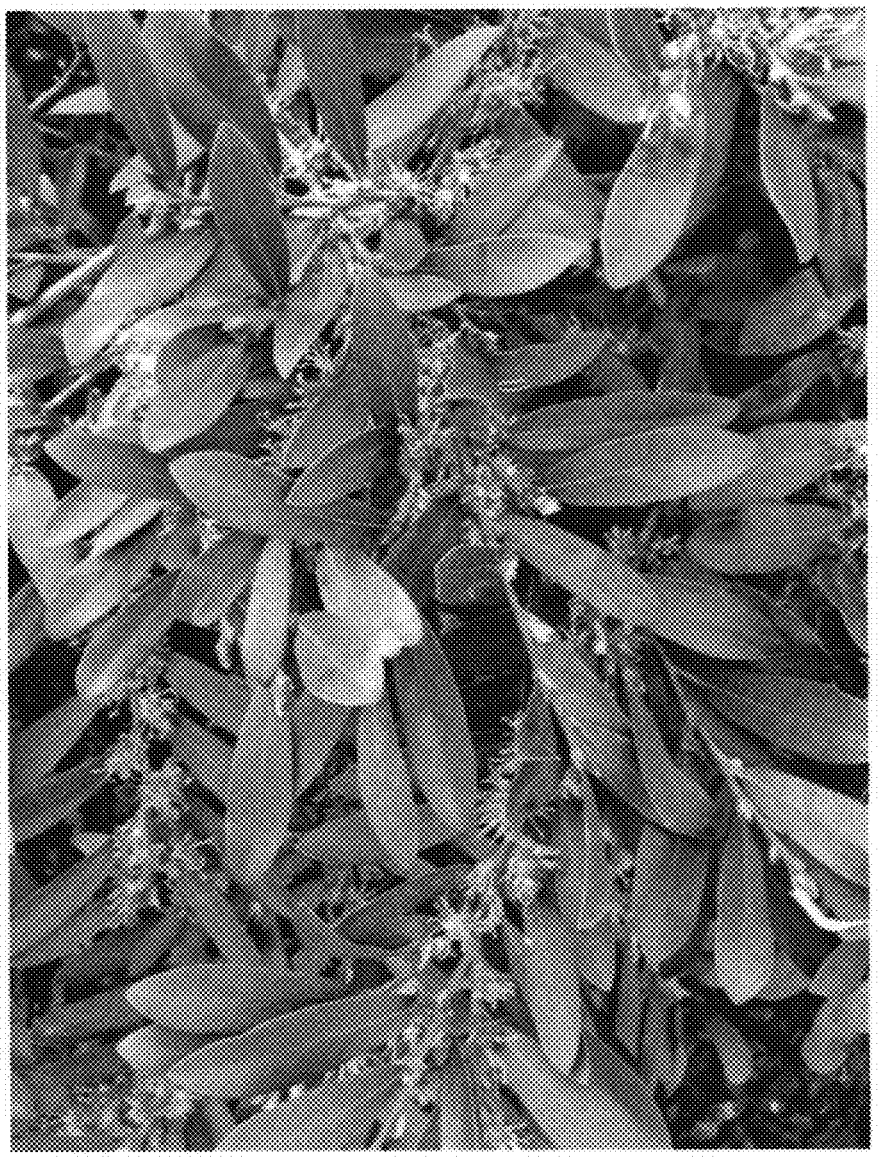

* * * * *